US00PP36822P2

(12) United States Plant Patent
Nelson et al.

(10) Patent No.: US PP36,822 P2
(45) Date of Patent: Jul. 15, 2025

(54) STRAWBERRY PLANT NAMED 'BG-15.490.061'

(50) Latin Name: *Fragaria ananassa*
Varietal Denomination: BG-15.490.061

(71) Applicant: BERRY GENETICS, INC., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: Berry Genetics, Inc., Freedom, CA (US)

( * ) Notice: Subject to any disclaimer, the term of this patent is extended or adjusted under 35 U.S.C. 154(b) by 0 days.

(21) Appl. No.: 18/807,104

(22) Filed: Aug. 16, 2024

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ..... A01H 6/7409; A01H 5/08
See application file for complete search history.

(56) References Cited

U.S. PATENT DOCUMENTS

PP23,255 P2 12/2012 Nelson et al.
PP25,865 P3 9/2015 Nelson et al.

*Primary Examiner* — Keith O. Robinson
(74) *Attorney, Agent, or Firm* — FOLEY & LARDNER LLP

(57) ABSTRACT

This invention relates to a new and distinct variety of strawberry plant named 'BG-15.490.061'. This new strawberry plant named 'BG-15.490.061' is primarily adapted to the growing conditions of the central coast of California, and is primarily characterized by its orange red to red fruit color, medium fruit size, conical fruit shape, with slight differences between primaries and secondaries; fair fruit flavor, with seeds typically held even the surface; medium to large plant size, with medium plant density; medium yellow green foliage color, with slightly concave to flat cross section; and fruiting trusses typically held even to below the plant, with little to no anthocyanins and weak pubescence.

5 Drawing Sheets

Latin name of the genus and species of the plant claimed: *Fragaria ananassa.*
Variety denomination: 'BG-15.490.061'.

BACKGROUND OF THE INVENTION

The present invention relates to a new and distinct strawberry variety named 'BG-15.490.061'. This new variety is a result of a controlled cross made in 2015 in an ongoing breeding program between strawberry variety designated 'BG-4316' (U.S. Plant Pat. No. 23,255) as the seed (female) parent, and strawberry variety designated 'BG-7.3065' (unpatented) as the pollen (male) parent. The variety is botanically known as *Fragaria ananassa.*

The seedling resulting from the aforementioned cross was selected from a controlled breeding plot in Ventura County, California in the spring of 2017. After its selection, the new variety was asexually propagated by stolons in both Siskiyou County, California and San Joaquin County, California. The new variety was extensively tested over the next several years in fruiting fields in Ventura County, California. This propagation has demonstrated that the combination of traits disclosed herein as characterizing the new variety are fixed and remain true-to-type through successive generations of asexual reproduction.

BRIEF SUMMARY OF THE INVENTION

'BG-15.490.061' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'BG-15.490.061', which in combination distinguish this strawberry plant as a new and distinct variety:

1. Fruit is orange red to red in color, medium in size, conical in shape, with slight differences between primaries and secondaries;
2. Fruit is fair in flavor, with seeds typically held even the surface;
3. Plant is medium to large in size, with medium density;
4. Foliage is medium yellow green in color, and slightly concave to flat in cross section; and
5. Fruiting trusses are typically held even to below the plant, with little to no anthocyanins and weak pubescence.

The strawberry variety that is believed to be most closely related to the new variety 'BG-15.490.061' is 'BG-4.367' (U.S. Plant Pat. No. 25,865). In side-by-side comparisons to the similar strawberry variety 'BG-4.367', 'BG-15.490.061' differs by the following combination of characteristics as described in Table 1.

TABLE 1

| Characteristic | 'BG-15.490.061' | 'BG-4.367' (U.S. Plant Pat. No. 25,865) |
|---|---|---|
| Fruit: color | Ranges from orange red to red | Red |
| Fruit: average size | Medium | Large |
| Fruit: flesh firmness | Firm | Very firm |
| Time of flowering | Medium | Early |
| Plant: vigor | Ranges from medium to large | Medium |
| Foliage: shape in cross section | Slightly concave to flat | Strongly concave |
| Fruiting truss: position relative to foliage | Ranges from level with to beneath | Ranges from level with to above |
| Disease: Fusarium wilt | Susceptible | Resistant |

For identification, a series of molecular markers have been determined for this new variety.

'BG-15.490.061' differs from its parents, 'BG-4316' and 'BG-7.3065' by the following combination of characteristics as described in Tables 2 and 3.

TABLE 2

| Characteristic | 'BG-15.490.061' | 'BG-4316' (U.S. Plant Pat. No. 23,255) |
|---|---|---|
| Plant: size | Ranges from medium to large | Medium |
| Fruit: color | Ranges from orange to orange red | Orange red |
| Fruit: sweetness | Fair | Good |
| Disease: Fusarium wilt | Susceptible | Moderately resistant |

TABLE 3

| Characteristic | 'BG-15.490.061' | 'BG-7.3065' (UNPATENTED) |
|---|---|---|
| Fruit: sweetness | Fair | Good |
| Fruit: shape | Conical | Long conic |
| Fruit: flesh firmness | Firm | Very firm |
| Disease: Fusarium wilt | Susceptible | Resistant |

BRIEF DESCRIPTIONS OF THE PHOTOGRAPHS

The accompanying color photographs illustrate the overall appearance of typical specimens of the new strawberry variety 'BG-15.490.061' at various stages of development, as true as it is reasonably possible with color reproductions of this type. Color in the photographs may differ slightly from the color value cited in the botanical descriptions which accurately describe the color of 'BG-15.490.061'. The depicted plant and plant parts of the new strawberry variety 'BG-15.490.061' are approximately five to seven months old. The photographs were taken in Ventura County, California.

DETAILED BOTANICAL DESCRIPTION

Figure 1:
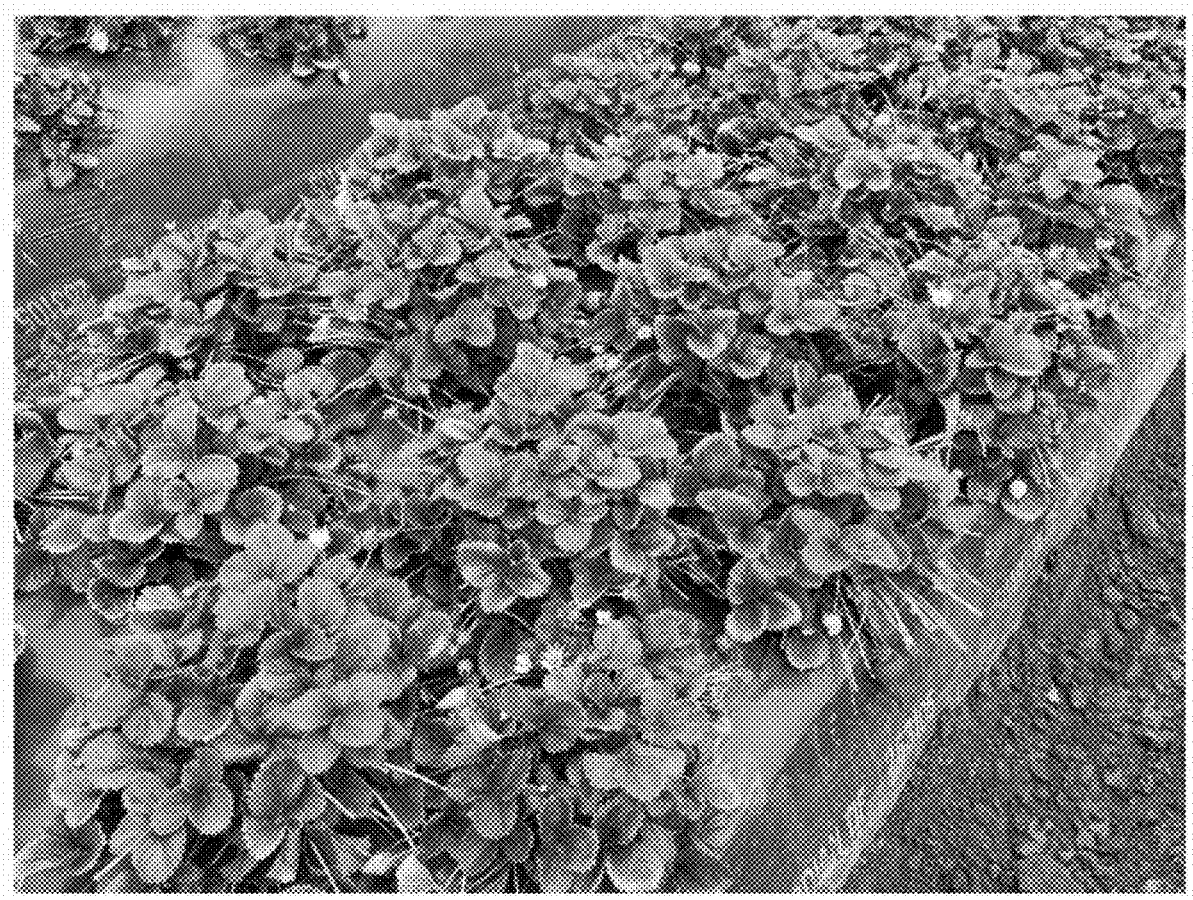
FIG. 1 shows fruiting field characteristics of 'BG-15.490.061', taken in the month of April 2024.
Figure 2:
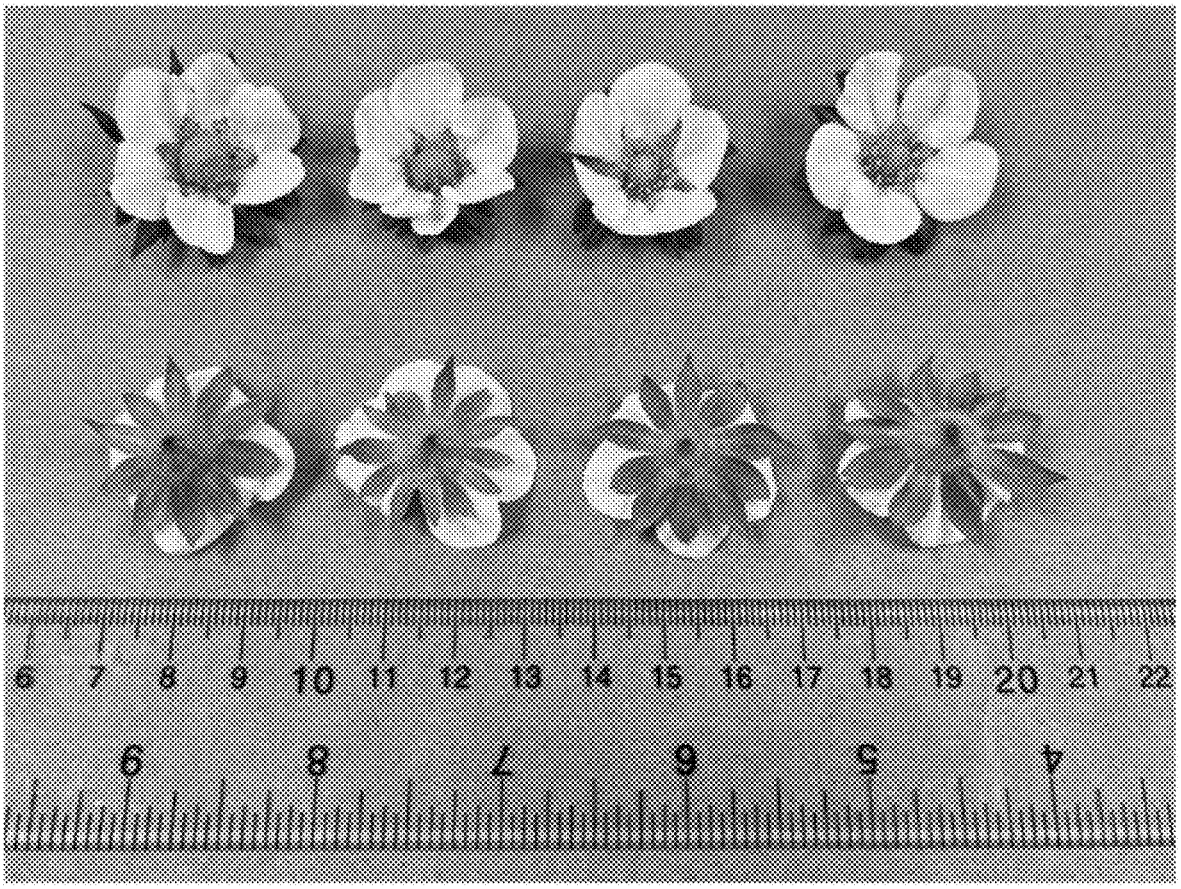
FIG. 2 shows upper and lower surfaces of flower and flower parts of 'BG-15.490.061', taken in the month of April 2024.
Figure 3:
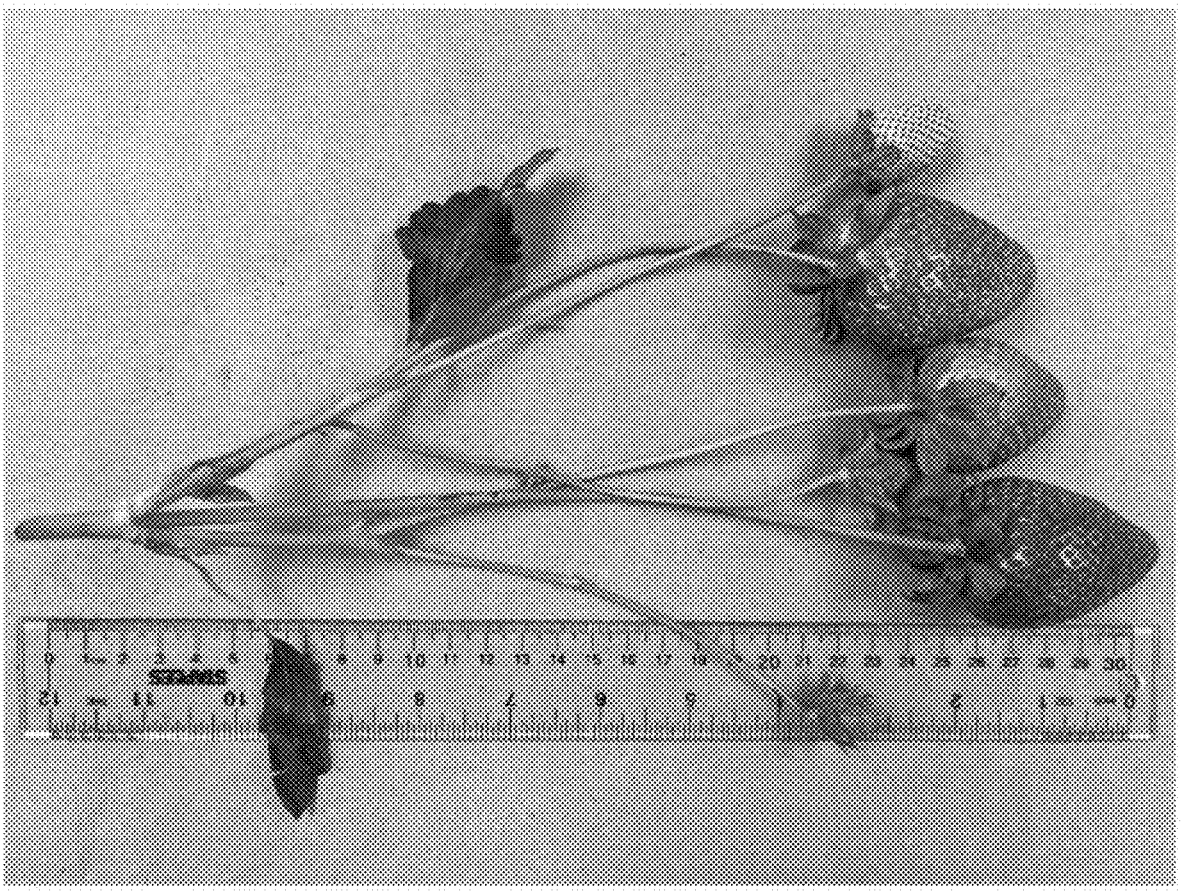
FIG. 3 shows typical fruiting truss and truss parts of 'BG-15.490.061', taken in the month of April 2024.
Figure 4:
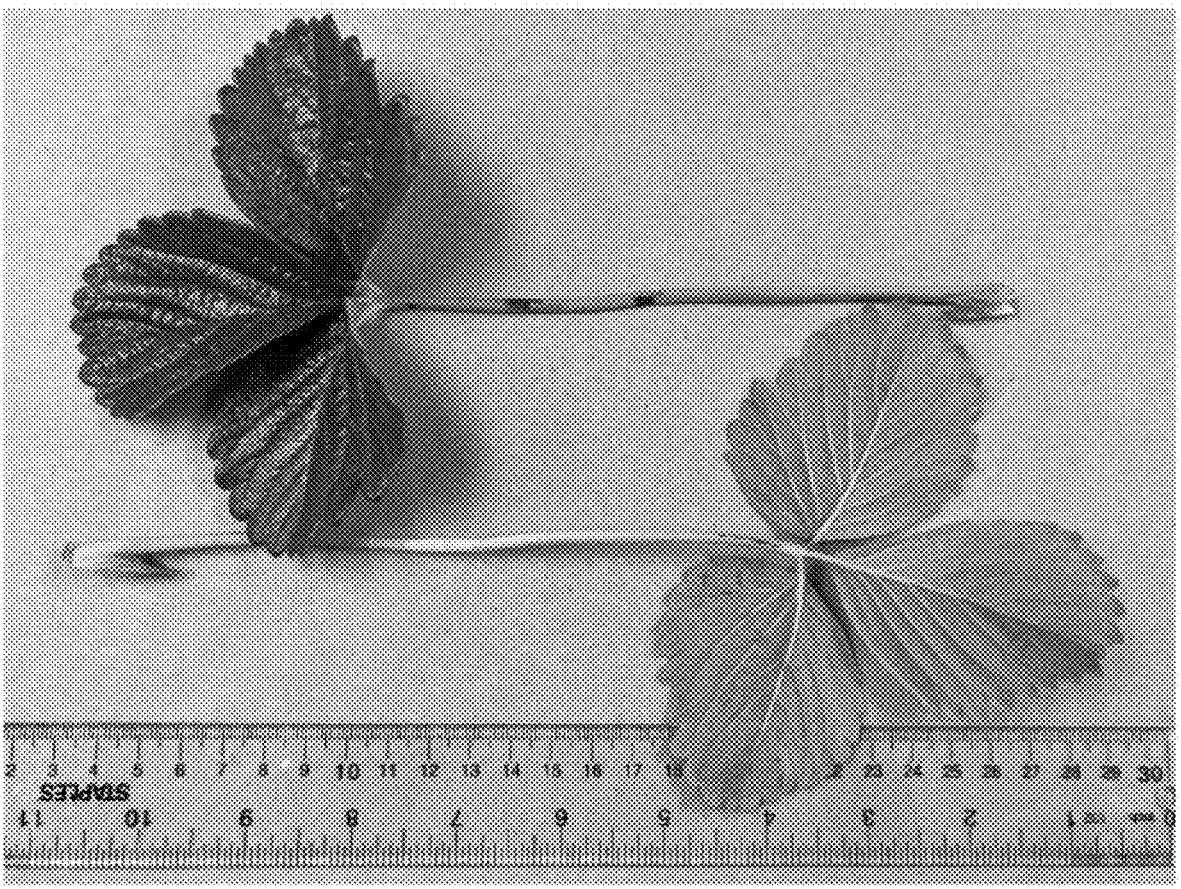
FIG. 4 shows upper and lower surfaces of leaf and leaf parts of 'BG-15.490.061', taken in the month of April 2024.
Figure 5:
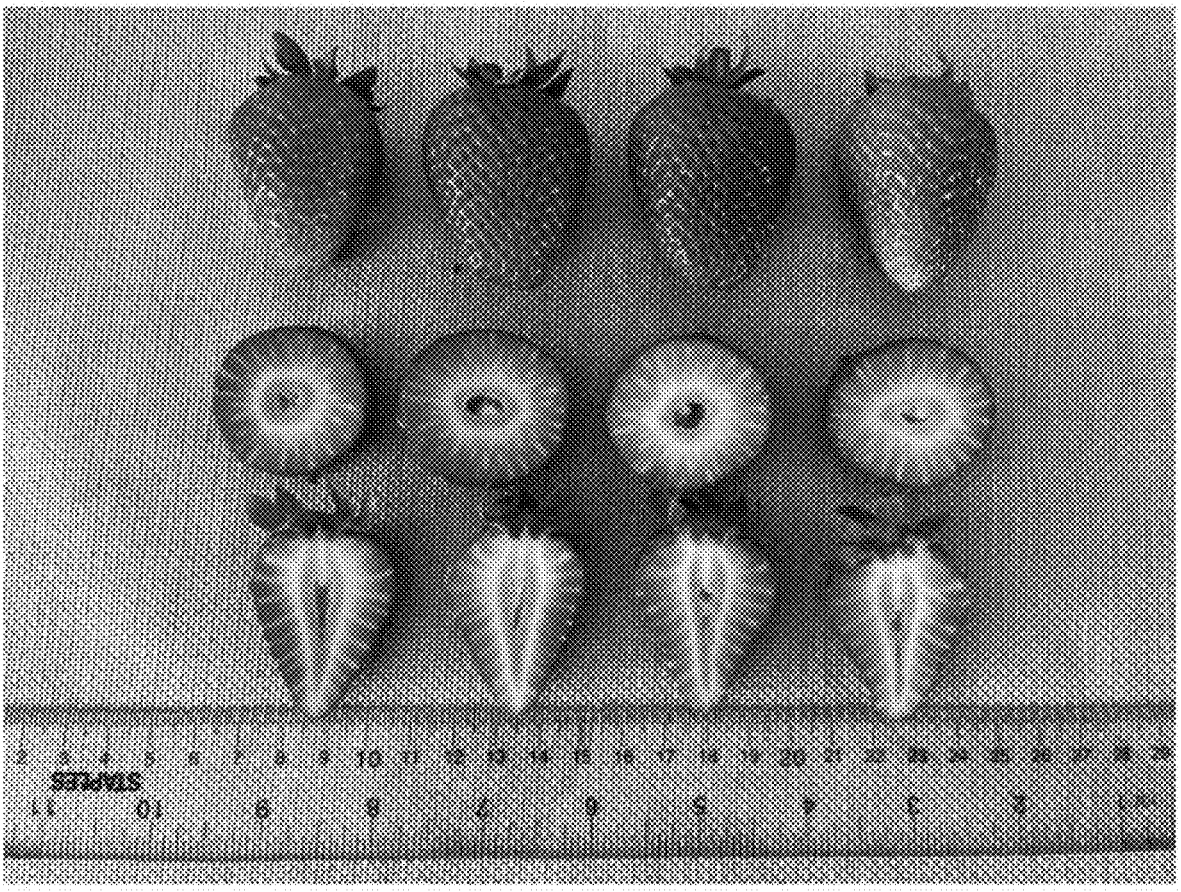
FIG. 5 shows internal and external mature fruit characteristics of 'BG-15.490.061', taken in the month of May 2024.

The new variety 'BG-15.490.061' has not been observed under all possible environmental conditions. The characteristics of the new variety 'BG-15.490.061' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'BG-15.490.061', unless otherwise noted, are based on observations taken during the 2024 growing season in Ventura County, California. These measurements and ratings were taken from plants of 'BG-15.490.061' dug from a high-elevation nursery located in Siskiyou County, California during early October 2023 and planted approximately four to five days later in Ventura County, California. The approximate age of the observed plants is five to six months. Yield observations including average weight and marketable yield, along with fruit quality characteristics including soluble solids, are averaged from three years of data collected from the 2022 through 2024 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London, Sixth Edition (2019 Reprint).

The following characteristics describe fruit, plant, stolon, foliage, fruiting truss, flower, reproductive organs and pest and disease characteristics of the new strawberry 'BG-15.490.061'.

Fruit characteristics:

*Color of mature fruit*.—RHS N34C (orange red to red).
*Color of internal flesh* (*excluding core*).—RHS 34B (light red).
*Color of core*.—RHS 34C (light red).
*Average length* (*cm*).—4.6.
*Average width* (*cm*).—3.7.
*Size*.—Medium.
*Average length/width ratio*.—1.25 (slightly longer than broad).
*Hollow center average length* (*mm*).—19.4.
*Hollow center average width* (*mm*).—5.7.
*Hollow center expression*.—Weak.
*Season average weight* (*gm*).—29.2.
*Marketable yield season* (*gm/plant*).—1,273.
*Predominant shape*.—Conical.
*Difference in shape between primary and secondary fruit*.—Slight.
*Band without achenes*.—Narrow.
*Evenness of surface*.—Even or very slightly uneven.
*Evenness of color*.—Even or very slightly uneven.

*Glossiness*.—Medium.
*Insertion of achenes*.—Level with surface.
*Average calyx diameter* (*cm*).—3.7.
*Position of calyx attachment*.—Ranges from inserted to level.
*Attitude of sepals*.—Ranges from outward to upward.
*Size of calyx in relation to fruit diameter*.—Same size.
*Adherence of calyx* (*when fully ripe*).—Strong.
*Firmness of flesh*.—Firm.
*Keeping quality*.—Good.
*Fruit market*.—Fresh.
*Post-harvest fruit longevity* (*at* 1 *to* 3 *degrees Celsius*).—7 to 10 days.
*Distribution of red color of the flesh*.—Marginal and central.
*Sweetness*.—Fair.
*Soluble solids* (% *Brix*).—6.9.
*Achene color, shaded side*.—RHS 153C (yellow green group).
*Achene color, sun-exposed side*.—RHS 184A (greyed purple group).
*Achene average length* (*mm*).—1.5.
*Achene average width* (*mm*).—0.8.
*Achene average weight* (*mg*).—0.5.
*Achene average quantity per berry*.—438.
*Achene shape*.—Elliptic.
*Time of beginning of flowering*.—Medium (early December in Ventura County, California).
*Time of beginning of fruit ripening*.—Medium (late December in Ventura County, California).
*Flowering season*.—December to May (in Ventura County, California).
*Harvest season*.—December to June (in Ventura County, California).
*Harvest maturity*.—Mid (April in Ventura County, California).
*Plant hardiness*.—Zone 10 (USDA Plant Hardiness Zone Map).
*Type of bearing*.—Not remontant (short-day).

Plant characteristics:
*Average height* (*cm*).—20.3.
*Average spread* (*cm*).—33.5.
*Size*.—Ranges from medium to large.
*Habit*.—Semi-upright.
*Density*.—Medium.
*Vigor*.—Medium.

Stolon characteristics:
*Color*.—RHS N144C (yellow green group).
*Anthocyanin coloration*.—RHS 181D (greyed red group).
*Anthocyanin intensity*.—Absent or very weak.
*Pubescence*.—Medium.
*Attitude of hairs*.—Upward.
*Average quantity in nursery* (*per square foot*).—7 to 9 (medium).
*Average diameter at first bract* (*mm*).—3.6 (ranges from medium to thick).
*Length from mother plant to first daughter* (*cm*).—29.8.

Terminal leaf characteristics:
*Average length* (*cm*).—6.6.
*Average width* (*cm*).—5.7.
*Average area terminal* ($cm^2$).—37.3.
*Average length/width ratio*.—1.16 (longer than broad).
*Shape of base*.—Obtuse.
*Shape of apex*.—Obtuse.
*Margins* (*shape of teeth*).—Obtuse (serrate to crenate).
*Average serrations per leaf*.—17.8.

Foliage characteristics:
*Color of upper surface*.—RHS 137A (medium yellow green).
*Color of lower surface*.—138B (green group).
*Color of venation, upper surface*.—RHS 137D (green group).
*Color of venation, lower surface*.—RHS 147D (yellow green group).
*Number of leaflets*.—3-4.
*Foliage size*.—Medium.
*Average length* (*cm*).—10.3.
*Average width* (*cm*).—12.8.
*Average area foliage* ($cm^2$).—131.2.
*Shape in cross section*.—Slightly concave to flat.
*Interveinal blistering*.—Medium.
*Pubescence of upper surface*.—Light.
*Pubescence of lower surface*.—Light.
*Venation pattern*.—Pinnate reticulate.
*Leaf glossiness*.—Medium.
*Leaf variegation*.—Absent.
*Leaf rugosity*.—Medium.

Petiole characteristics:
*Petiole color*.—RHS 146D (yellow green group).
*Average length* (*cm*).—14.6.
*Average diameter* (*mm*).—3.0.
*Average size*.—Medium.
*Attitude of hairs*.—Slightly outward.
*Frequency of bract leaflets*.—0% occurrence (none).
*Size of bract leaflets*.—N/A.
*Pubescence*.—Moderate.
*Petiolule color*.—RHS 146D (yellow green group).
*Petiolule average length* (*mm*).—5.8.
*Petiolule average diameter* (*mm*).—1.4.

Stipule characteristics:
*Color*.—RHS 145B (yellow green group).
*Anthocyanin coloration*.—RHS 63A (red purple group).
*Anthocyanin intensity*.—Ranges from medium to strong.
*Average length* (*mm*).—11.7.
*Average width* (*mm*).—9.3.
*Shape*.—Triangular.
*Pubescence*.—Light.
*Shape of base*.—N/A.
*Shape of apex*.—Acuminate.
*Margins*.—Entire.

Fruiting truss characteristics:
*Anthocyanin coloration*.—RHS 179B (greyed red group).
*Anthocyanin intensity*.—Absent or very weak.
*Average length at maturity* (*cm*).—24.0.
*Position relative to foliage*.—Ranges from beneath to level with.
*Flower quantity* (*season average per plant*).—50 to 60 (ranges from medium to many).
*Average fruit quantity per truss*.—6.1 (medium).
*Attitude at first pick*.—Prostrate.
*Primary pedicel color*.—RHS 144A (yellow green group).
*Primary pedicel average length* (*cm*).—19.2.
*Primary pedicel average diameter* (*mm*).—2.9.
*Pedicel attitude of hairs*.—Upward.
*Pedicel pubescence*.—Weak.

*Primary peduncle color*.—RHS 144A (yellow green group).
*Primary peduncle average length* (*cm*).—2.0.
*Primary peduncle average diameter* (*mm*).—6.9.
*Peduncle pubescence*.—Medium.

Flower characteristics:
*Petal color, upper surface*.—RHS NN155C (white group).
*Petal color, lower surface*.—RHS NN155C (white group).
*Petal average length* (*mm*).—12.5.
*Petal average width* (*mm*).—12.5.
*Petal average length/width ratio*.—1.0 (as long as broad).
*Average petal quantity per flower*.—5.9.
*Petal shape*.—Obovate.
*Petal pubescence*.—Smooth.
*Petal shape of base*.—Obtuse.
*Petal shape of apex*.—Rounded.
*Petal margins*.—Entire.
*Sepal color, upper surface*.—RHS NN137C (green group).
*Sepal color, lower surface*.—RHS 138B (green group).
*Sepal average length* (*mm*).—11.2.
*Sepal average width* (*mm*).—4.6.
*Sepal average length/width ratio*.—2.45.
*Average sepal quantity per flower*.—11.5.
*Sepal shape*.—Elliptical.
*Sepal pubescence*.—Light.
*Sepal shape of apex*.—Acuminate.
*Sepal margins*.—Entire.
*Flower bud color*.—RHS 145B (yellow green group).
*Flower bud shape*.—Cup.
*Flower bud average length* (*mm*).—15.6.
*Flower bud average diameter* (*mm*).—8.9.
*Corolla average diameter* (*mm*).—32.3 (large).
*Flower average depth* (*mm*).—12.8 (medium).
*Calyx average diameter* (*mm*).—31.1.
*Size of calyx relative to corolla*.—Same size.
*Arrangement of petals*.—Ranges from touching to overlapping.
*Size of inner calyx relative to outer calyx*.—Ranges from smaller to same.

Reproductive organs:
*Anther color*.—RHS 13A (yellow orange group).
*Filament color*.—RHS 145C (yellow green group).
*Stamen*.—Present.
*Filament average length* (*mm*).—2.4.
*Anther average length* (*mm*).—1.3.
*Anther average width* (*mm*).—0.8.
*Anther shape*.—Elliptic.
*Pollen amount*.—Abundant.
*Pollen color*.—RHS 13A (yellow orange group).
*Ovary color*.—RHS 147C (yellow green group).
*Style color*.—RHS 151D (yellow green group).
*Pistil average quantity per flower*.—438.
*Pistil average length* (*mm*).—1.7.
*Style average length* (*mm*).—1.4.
*Stigma average diameter* (*mm*).—0.3.
*Stigma shape*.—Rounded.

Disease and pest reactions:
*Powdery mildew* (*Sphaerotheca macularis*).—Moderate.
*Botrytis fruit rot* (*Botrytis cinerea*).—Moderately susceptible.
*Fusarium wilt* (*Fusarium oxysporum*).—Susceptible.
*Two-spotted spider mite* (*Tetranychus urticae*).—Moderately susceptible.

We claim:

1. A new and distinct strawberry plant named 'BG-15.490.061', as herein described and illustrated.

* * * * *